United States Patent
Rosocha et al.

(10) Patent No.: US 10,526,262 B2
(45) Date of Patent: Jan. 7, 2020

(54) PROCESS TO MAKE HIGHLY SUBSTITUTED INDENES USING METAL SALT CATALYSTS

(71) Applicant: Gregory Rosocha, Toronto (CA)

(72) Inventors: Gregory Rosocha, Toronto (CA); Robert Batey, Toronto (CA)

(*) Notice: Subject to any disclaimer, the term of this patent is extended or adjusted under 35 U.S.C. 154(b) by 65 days.

(21) Appl. No.: 14/437,628

(22) PCT Filed: Oct. 24, 2012

(86) PCT No.: PCT/IB2012/002074
§ 371 (c)(1),
(2) Date: Apr. 22, 2015

(87) PCT Pub. No.: WO2014/064477
PCT Pub. Date: May 1, 2014

(65) Prior Publication Data
US 2015/0274617 A1   Oct. 1, 2015

(51) Int. Cl.
| | | |
|---|---|---|
| *C07C 17/23* | (2006.01) | |
| *C07C 23/18* | (2006.01) | |
| *C07C 25/22* | (2006.01) | |
| *C07C 201/12* | (2006.01) | |
| *C07C 253/30* | (2006.01) | |
| *C07C 2/86* | (2006.01) | |
| *C07D 217/04* | (2006.01) | |
| *C07D 471/06* | (2006.01) | |

(52) U.S. Cl.
CPC .............. *C07C 23/18* (2013.01); *C07C 2/861* (2013.01); *C07C 17/23* (2013.01); *C07C 25/22* (2013.01); *C07C 201/12* (2013.01); *C07C 253/30* (2013.01); *C07D 217/04* (2013.01); *C07D 471/06* (2013.01); *C07C 2602/08* (2017.05)

(58) Field of Classification Search
CPC ....... C07C 17/23; C07C 2/861; C07C 201/12; C07C 23/18; C07C 25/22; C07C 253/30; C07C 2102/08; C07D 217/04; C07D 471/06
See application file for complete search history.

(56) References Cited

U.S. PATENT DOCUMENTS 7,703,485 B2 * 4/2010 Rodewald ........... B01L 3/50825
141/329

OTHER PUBLICATIONS

Kostikov, R. R. et al. Zhurnal Organicheskoi Khimii, "Study of thermal transformations of gem-dihalodiphenylcyclopropanes" vol. 19, Issue:8, pp. 1625-1632, Journal, 1983; Abstract only.*
Olah, G. A. et al. "Preparative carbocation chemistry. IV. Improved preparation of triphenylcarbenium (trityl) salts" Synthesis (1972), (10), 544; ; Abstract only.*
Sigma-Aldrich ("Silver tetrafluoroborate" Available Date: Jul. 12, 2007).*

(Continued)

*Primary Examiner* — Medhanit W Bahta
(74) *Attorney, Agent, or Firm* — Chumak & Company LLP; Yuri Chumak

(57) ABSTRACT

According to embodiments described in the specification, a chemical process includes the steps of reacting a chemical reaction fluid including a solvent, 1,2-biaryl gem-dibromo-cyclopropane or 1,2-biphenyl-gem-dibromocyclopropane, and a metal salt including a silver tetrafluoroborate salt at low temperatures to make 1-phenyl-2-bromo indenes in a vessel that is capable of being closed.

38 Claims, 6 Drawing Sheets

(56) References Cited

OTHER PUBLICATIONS

Sigma-Aldrich ("1,2-dichloroethane" Available Date: May 13, 2009).*
Rosocha, Y. G. et al. "Development and Investigation of Electrocyclization Reactions Leading Towards Indene and Thiatriazole Formation and their Functionalization". A thesis submitted in conformity with the requirements for the degree of Doctor of Philosophy Department of Chemistry University of Toronto; 2011, pp. 1-509.*
Watts, P. et al. "The application of micro reactors for organic synthesis" Chem. Soc. Rev., 2005, 34, 235-246.*

* cited by examiner

| Indene | Name<br>Chemical Formula<br>Molar Mass<br>(g/mol) | Yield<br>(%) |
|---|---|---|
| <br>8 | 2-bromo-1-phenyl indene<br>$C_{15}H_{11}Br$<br>270.15 | 95 |
| <br>9 | 2-bromo-1-(p-tolyl)-1H-indene<br>$C_{16}H_{13}Br$<br>285.18 | 97 |
| <br>10 | 2-bromo-5,7-dimethyl-1-phenyl-1H-indene<br>$C_{17}H_{15}Br$<br>299.21 | 92 |
| <br>11 | 2-bromo-1-(3,5-dimethylphenyl)-1H-indene<br>$C_{17}H_{15}Br$<br>299.21 | 92 |
| <br>12 | 2-bromo-3-(p-tolyl)-1H-indene<br>$C_{16}H_{13}Br$<br>285.18 | 97* |

| Indene | Name<br>Chemical Formula<br>Molar Mass<br>(g/mol) | Yield<br>(%) |
|---|---|---|
| <br>13 | 2-bromo-3-phenyl-1H-indene<br>$C_{15}H_{11}Br$<br>271.16 | 85* |
| <br>14 | 2-bromo-6-methyl-1-phenyl-1H-indene<br>$C_{16}H_{13}Br$<br>285.18 | 97 |
| <br>15 | 2-bromo-1-(3-nitrophenyl)-1H-indene<br>$C_{15}H_{10}BrNO_2$<br>316.15 | 75 |
| <br>16 | 2-bromo-7-methyl-1-(m-tolyl)-1H-indene<br>$C_{17}H_{15}Br$<br>299.21 | 99 |
| <br>17 | 2-bromo-5-methyl-1-(m-tolyl)-1H-indene<br>$C_{17}H_{15}Br$<br>299.21 | 99 |

| Indene | Name<br>Chemical Formula<br>Molar Mass<br>(g/mol) | Yield<br>(%) |
|---|---|---|
| <br>18 | 2-bromo-3-(3-nitrophenyl)-1H-indene<br>$C_{15}H_{10}BrNO_2$<br>316.15 | 70* |
| <br>19 | 2-bromo-3-(4-nitrophenyl)-1H-indene<br>$C_{15}H_{10}BrNO_2$<br>316.15 | 90* |
| <br>20 | 2-bromo-5-chloro-3-(4-chlorophenyl)-1H-indene<br>$C_{15}H_9BrCl_2$<br>340.04 | 94* |
| <br>21 | 2-bromo-7-chloro-3-(2-chlorophenyl)-1H-indene<br>$C_{15}H_9BrCl_2$<br>340.04 | 99* |
| <br>22 | 2-bromo-6-methyl-1-(p-tolyl)-1H-indene<br>$C_{17}H_{15}Br$<br>299.21 | 86 |

| Indene | Name<br>Chemical Formula<br>Molar Mass<br>(g/mol) | Yield<br>(%) |
|---|---|---|
| 23  | 2-bromo-6-chloro-1-(4-chlorophenyl)-1H-indene<br>$C_{15}H_9BrCl_2$<br>340.04 | 91 |
| 24  | 2-bromo-4-chloro-1-(2-chlorophenyl)-1H-indene<br>$C_{15}H_9BrCl_2$<br>340.04 | 93 |

PROCESS TO MAKE HIGHLY SUBSTITUTED INDENES USING METAL SALT CATALYSTS

FIELD OF TECHNOLOGY

The present disclosure relates to a process of making highly substituted indenes using silver salts and, in particular, a process of making highly substituted indenes from gem-dibromocyclopropanes with silver salts using a batch method and micro flow reactor method.

BACKGROUND

Indenes are important compounds and are useful chemicals to make pharmaceutical medicaments or other important industrial chemicals such as plastics and resins. In addition, indenes have been used in research and development to make pharmaceutical medicaments. For example, indenes and their pharmaceutical preparations can be used as medicaments for the treatment of obesity, liver and cancer. PCT/KR2005/001051 discloses a process to make indenes that can be used to modulate the peroxisome proliferator activator receptor (PPAR) to treat many diseases. However, the process has many steps and uses toxic chemicals that can have high research and development costs and high manufacturing costs. These methods use very acidic and toxic chemicals that can pose a hazard for personnel working with the chemicals which are extremely dangerous. It is desirable to provide a process that does not use corrosive chemicals and that is useful for making substituted indenes that can be used as medicaments or high value chemicals for use by different industries.

DETAILED DESCRIPTION

Figure 1:
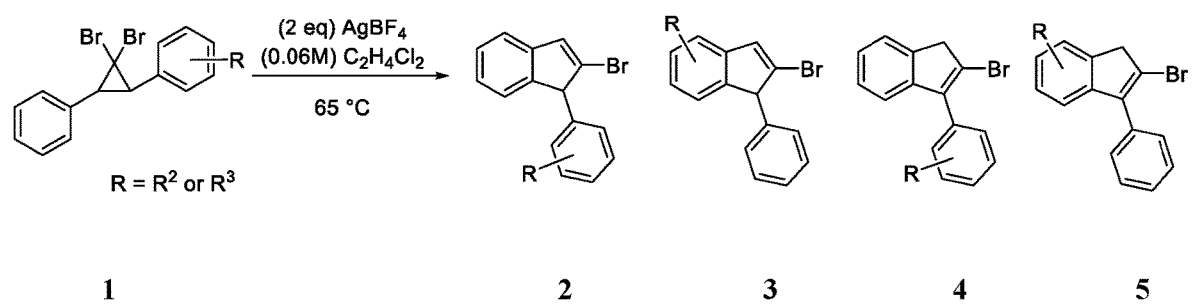
FIG. 1 illustrates an exemplary reaction to make highly substituted 2-bromo-1-phenyl indenes from unsymmetric gem-dihalocyclopropanes in accordance with the present specification.
Figure 2:
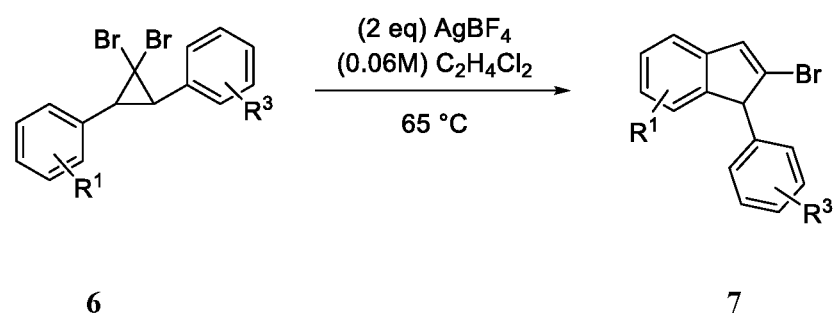
FIG. 2 illustrates synthesis of 2-bromoindenes from symmetric gem-dihalocyclopropanes in accordance with an example of the present specification.
Figure 3:
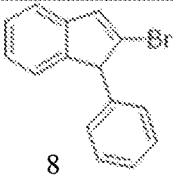
FIG. 3 to FIG. 6 show example reactions to make highly substituted 2-bromo-1-phenyl indenes synthesized from gem-dihalocyclopropanes in accordance with the present specification.
Figure 3:
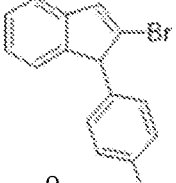
Figure 3:
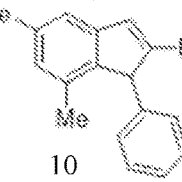
Figure 3:
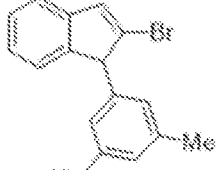
Figure 3:
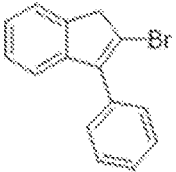
Figure 4:
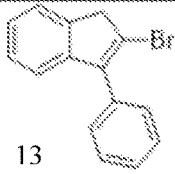
Figure 4:
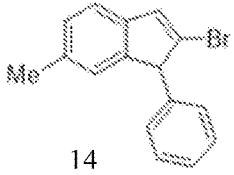
Figure 4:
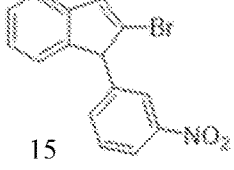
Figure 4:
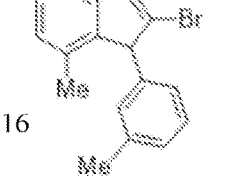
Figure 4:
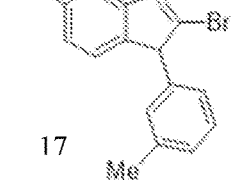
Figure 5:
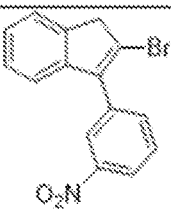
Figure 5:
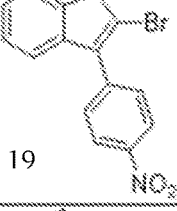
Figure 5:
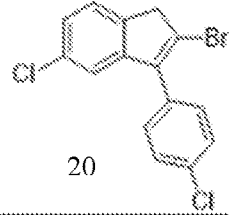
Figure 5:
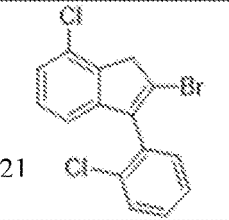
Figure 5:
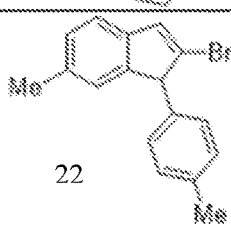
Figure 6:
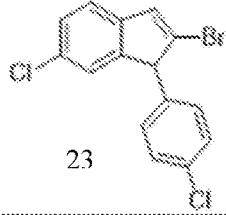
Figure 6:
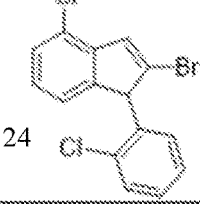

The following describes a chemical process including the steps of reacting a chemical reaction fluid including a solvent, 1,2-biaryl gem-dibromocyclopropane or 1,2-biphenyl-gemdibromocyclopropane, and a metal salt including a silver tetrafluoroborate salt to make 1-phenyl-2-bromo indenes in a vessel that is capable of being closed.

Examples in accordance with the present specification offer benefits to customers through increases in efficiency and safety, and decreases in waste byproducts.

According to one example, the present specification is directed to synthesis of 2-bromo-indenes (1-4) from the corresponding 1,2-biaryl gem-dihalocyclopropanes using silver tetrafluoroborate in 1,2-dichloroethane at 65° C.

It has been observed that other processes and/or protocols do not exist to synthesize highly 1,2-substituted indenes involving the use of silver salts. Typically, other methods involve the use of very strong acids which are very hazardous due to their corrosive nature or toxic metal catalysts.

Processes of the present specification involve an electrocyclization cascade mechanism which is a very efficient high-yielding reaction and has not been used for the synthesis of indenes.

The final products are part of a chemical class of indenes which has been shown to possess many desirable medicinal properties such as anticancer, insulin modulators, cardiovascular, anti-obesity, etc. They have similar core structures as in the D vitamins.

Indenes are naturally occurring compounds isolated from coal tar fractions/crude oil refining. The main uses of indenes are for the production of indene resin which is the starting point for many plastic products (i.e., floor tiles). Indenes are also used as thermal imaging material for stenciling. Indenes have been shown to possess many desirable properties and are also biologically active used as pesticides imbedded in plastic animal collars. Indenes are available pharmaceuticals for the treatment of HIV (Crixivan-Merck, $275 million/2008 annual revenue) and pain (Sulindac). Applications for indenes extend to:
1. Treatment of cerebral vascular disease—Indeloxazine (Japan).
2. Estrogen receptor agonists.
3. Selective modulators for the peroxisome proliferator activator receptor (PPAR).
4. Anti-inflammatory pharmaceutical agents—(Sulindac-Clinoril-Merck US and UK).
5. Antifungal agents.
6. Treatment of precancerous and cancerous lesions.
7. Muscarinic agonists (Eli Lilly) (via osmium catalysis)
8. Anticoagulants.

The present specification is also directed to a microreactor flow device (also referred to as microreactors) capable of performing the above processes. Use of a microreactor flow device is advantageous for several reasons including that these microreactor flow devices have been shown to be more efficient than conventional batch synthesis by having the ability to increase in reaction efficiency by minimizing waste byproducts. As well, microreactors have also been shown to allow chemical reactions to be completed in a faster time. And, microreactors can be fully automated and controlled by a computer that allows for quick optimization of a reaction by allowing to change variables such as temperature, flow rate, concentration, and time.

According to one example of the present specification, a microreactor is a small, compact, modular, reactor that has a chemical output that is constant (i.e., 1 g/1 min-1 g/h). To achieve large scale production the devices are "numbered up" instead of "scaling up" (i.e., 1 device makes 1 g/min, therefore after 24 h=1.44 kg, after 365 days=525.6 kg. If 50 devices were operational then 26.2 tons of product are achieved annually). Therefore due to the numbering up method, different synthetic procedures are not needed on the larger scale (i.e., typically a small batch scale synthesis (1 g) differs from the large scale (1 ton) synthesis of the same product because different materials will be needed due to potential hazards and safety considerations associated with using a large amount of that chemical. Manufacturers may have a process scale up team that is aware of such hazards associated with these chemicals that specializes with large production of pharmaceuticals and chemical building blocks). The microreactor device would not need a process scale-up team to implement large scale production of a drug or chemical.

Use of microreactors also allows for a large isoquinoline library and other similar products to be synthesized having the ability to access over 5 trillion isoquinoline products by varying the indene and amine starting materials. The process can be used for the generation of new lead compounds, the manufacturing of generic drugs, chemical building blocks, and their scale up.

There are several companies that are currently using flow microreactor systems. The H-Cube is a product sold by Thales-Nano. The H-Cube allows the user to carry out hydrogenations without the need for a hydrogen tank and can handle up to half a kilogram of material/day. The unit generates hydrogen via the electrolysis of water, collects the generated hydrogen, and uses it throughout the hydrogenation. The product has been shown to be very efficient giving better results than batch methods. In addition, the lack of a tank of hydrogen eliminates any explosive hazard which is a primary concern when carrying out hydrogenations. Further, the unit is computer interfaced allowing optimal conditions to be achieved automatically (i.e., temperature, flow rate, concentration, with respect to product yield). The H-Cube retails for about $60K US and has a new larger version that is capable of higher production volumes.

There are other companies that provide microreactor systems but they are not engineered for specific processes (i.e., a specific class of reaction like hydrogenations which the H-Cube is designed for.) but rather are available as a kit for the customer to use on their current chemistry and see if it adds a benefit to them.

Some large pharmaceutical companies use microreactor technology to synthesize building blocks for pharmaceuticals (i.e., Merck, Pfizer, Genentech, etc.). Lonza chemicals use microreactors for hydrogenations and dehydrations. UOP and FMC use flow reactors for hydrogen peroxide synthesis. Siemens-Axiva use microreactors for polyacrylamide synthesis. Bayer-Schering use microreactors for DAST fluorinations (methods to incorporate fluorine into a molecule) and steroid synthesis. Degussa chemicals use microreactors for chemical oxidations. Xi'on Company (China) uses microreactors to synthesize nitroglycerine. Merck uses microreactors for synthesis (Grignard reagents).

The present specification relates to a chemical process for the synthesis of substituted 2-bromo-indenes from the corresponding 1,2-biaryl gem-dihalocyclopropanes using metal salts such as silver tetrafluoroborate. The process uses 1,2-dichloroethane as a solvent and temperatures below 65° C. (FIG. 1). Several highly substituted indenes and their corresponding isomers can be made. The process of the present specification, as illustrated in FIG. 1 to FIG. 6) can be used to make highly substituted indenes that can be used as useful chemicals by several industries.

Examples of the present specification has resulted in the making of the following indenes from the corresponding gem-dibromo cyclopropanes. 2-Bromo-1-phenyl-1H-indene, 2-Bromo-5-methyl-1-(m-tolyl)-1H-indene and 2-Bromo-7-methyl-1-(m-tolyl)-1H-indene, 2-Bromo-4-chloro-1-(2-chlorophenyl)-1H-indene, 2-Bromo-6-methyl-1-(p-tolyl)-1H-indene, 2-Bromo-6-chloro-1-(4-chlorophenyl)-1H-indene, 2-Bromo-1-(p-tolyl)-1H-indene, and 2-Bromo-6-methyl-1-phenyl-1H-indene, 2-Bromo-5,7-dimethyl-1-phenyl-1H-indene, 2-Bromo-1-(3,5-dimethylphenyl)-1H-indene, 2-Bromo-3-(3-nitrophenyl)-1H-indene.

The invention claimed is:

1. A chemical process comprising the steps of reacting a chemical reaction fluid comprising a solvent, 1,2-biaryl gem-dibromocyclopropane or 1,2-biphenyl-gem-dibromocyclopropane, and a metal salt comprising a silver tetrafluoroborate salt at low temperatures to make 1-phenyl-2-bromo indenes in a vessel that is capable of being closed.

2. The chemical process of claim 1 wherein the 1,2-biaryl gem-dibromocyclopropane is synthesized from stilbene.

3. The chemical process of claim 1 wherein the 1,2-biaryl gem-dibromocyclopropane has a functional group comprising-chloro, nitro, or methyl on one aryl ring at any position.

4. The chemical process of claim 1 wherein the solvent is 1,2-dichloroethane.

5. The chemical process of claim 1 wherein the temperature for the chemical process is within the range of 0° C.-100° C.

6. The chemical process of claim 1 wherein the 1-phenyl-2-bromo indenes are formed selectively using 1,2-biaryl-gem-dibromocyclopropane and 1,2-biphenyl-gem-dibromocyclopropane in chemical yields ranging from 0.100%-99.9%.

7. The chemical process of claim 1 wherein a $2\pi$ electrocyclic ring opening followed by a $4\pi$ electrocyclic ring closing reaction forms an indene with different substitution patterns.

8. The chemical process of claim 1 wherein the 1-phenyl-2-bromo indenes are obtained at 65° C.

9. The chemical process of claim 1 wherein the vessel is a micro flow reactor used with metal salts to form indenes.

10. The chemical process of claim 1 wherein indenes that are made are used as medicaments or starting materials for medicaments.

11. The chemical process of claim 1 wherein the reaction vessel is any vessel that is capable of being sealed.

12. The chemical process of claim 1 wherein the reaction vessel is a micro flow reactor comprising pre-fabricated channels with dimensions ranging from 1 nanometer to 200 micrometers.

13. The chemical process of claim 12 wherein the micro flow reactor passes the chemical reaction fluid inside the channels.

14. The chemical process of claim 1 wherein the reaction vessel obtains temperature ranges from −150° C. to 1000° C.

15. The chemical process of claim 12 wherein the micro flow reactor controls and regulates the rate of chemical reaction fluid flow and the residence times within the prefabricated channels.

16. The chemical process of claim 12 wherein the chemical reaction fluid flow rate of the micro flow reactor is within the ranges of 0.0001 mL/minute-500 L/min.

17. The chemical process of claim 1 wherein the indenes are used as pharmaceutical preparations and medicaments for the treatment of cancer.

18. The chemical process of claim 1 wherein the indenes are used as pharmaceutical preparations and medicaments for the treatment of cardiovascular disease.

19. The chemical process of claim 1 wherein the indenes are used as pharmaceutical preparations and medicaments for the treatment of HIV.

20. The chemical process of claim 1 wherein the indenes are used as pharmaceutical preparations and medicaments for the treatment of obesity.

21. The chemical process of claim 1 wherein the indenes are used as pharmaceutical preparations and medicaments for the treatment of diabetes.

22. The chemical process of claim 1 wherein the 1,2-biaryl gem-dibromocyclopropane has no functional groups on both aryl rings.

23. The chemical process of claim 1 wherein 2-Bromo-1-phenyl-1H-indene is formed.

24. The chemical process of claim 1 wherein 2-Bromo-5-methyl-1-(m-tolyl)-1H-indene is formed.

25. The chemical process of claim 1 wherein 2-Bromo-7-methyl-1-(m-tolyl)-1H-indene is formed.

26. The chemical process of claim 1 wherein-2-Bromo-4-chloro-1-(2-chlorophenyl)-1H-indene is formed.

27. The chemical process of claim 1 wherein 2-Bromo-6-methyl-1-(p-tolyl)-1H-indene is formed.

28. The chemical process of claim 1 wherein 2-Bromo-6-chloro-1-(4-chlorophenyl)-1H-indene is formed.

29. The chemical process of claim 1 wherein 2-Bromo-1-(p-tolyl)-1H-indene is formed.

30. The chemical process of claim 1 wherein 2-Bromo-6-methyl-1-phenyl-1H-indene is formed.

31. The chemical process of claim 1 wherein 2-Bromo-5,7-dimethyl-1-phenyl-1H-indene is formed.

32. The chemical process of claim 1 wherein 2-Bromo-1-(3,5-dimethylphenyl)-1H-indene is formed.

33. The chemical process of claim 1 wherein 2-Bromo-3-(3-nitrophenyl)-1H-indene is formed.

34. The chemical process of claim 1 wherein the reaction vessel is selected from the group consisting of a batch reactor and a micro flow reactor.

35. The chemical process of claim 34 wherein the reaction vessel is a batch reactor.

36. The chemical process of claim 34 wherein the reaction vessel is a micro flow reactor.

37. The chemical process of claim 11 wherein the reaction vessel is a batch reactor.

38. The chemical process of claim 11 wherein the reaction vessel is a micro flow reactor.

* * * * *